United States Patent [19]

Martin-Smith

[11] Patent Number: 5,021,429

[45] Date of Patent: Jun. 4, 1991

[54] PHARMACOLOGICALLY ACTIVE AMINOALKYLPHENYL COMPOUNDS AND THEIR USE

[75] Inventor: Michael Martin-Smith, Ware, England

[73] Assignee: Allen & Hansburys Limited, England

[21] Appl. No.: 944,217

[22] Filed: Dec. 22, 1986

Related U.S. Application Data

[63] Continuation of Ser. No. 502,674, Jun. 9, 1983, abandoned, which is a continuation of Ser. No. 200,607, Oct. 24, 1980, abandoned, which is a continuation of Ser. No. 906,619, May 16, 1978, abandoned.

[30] Foreign Application Priority Data

May 17, 1977 [GB] United Kingdom ............... 20660/77
Sep. 27, 1977 [GB] United Kingdom ............... 40129/77

[51] Int. Cl.$^5$ .................. A61K 31/13; A61K 31/155; A61K 31/17; C07C 217/26
[52] U.S. Cl. .................... 514/331; 514/408; 514/586; 514/595; 514/605; 514/609; 514/610; 514/634; 514/644; 514/649; 514/651; 514/654; 514/655; 546/230; 546/231; 548/578; 564/27; 564/47; 564/99; 564/104; 564/108; 564/237; 564/299; 564/340; 564/341; 564/346; 564/353; 564/354; 564/367; 564/369
[58] Field of Search ................ 564/352, 353, 354, 27, 564/47, 99, 104, 108, 237, 299; 546/230, 231; 548/578; 514/331, 408, 586, 595, 605, 609, 610, 634, 644, 651

[56] References Cited

U.S. PATENT DOCUMENTS

| 3,814,750 | 6/1974 | Croso et al. ............... 564/346 X |
| 4,128,658 | 12/1978 | Price et al. ............... 544/152 X |
| 4,317,819 | 3/1982 | Clitherow et al. ............... 564/346 X |
| 4,522,943 | 6/1986 | Algeri et al. ............... 564/346 X |

OTHER PUBLICATIONS

Burger, "Medicinal Chemistry", 2nd Ed., pp. 79-81 (1970).
Burger (I), "Medicinal Chemistry", 3rd Ed. Part II, pp. 557-559 (1970).

Primary Examiner—Richard L. Raymond
Attorney, Agent, or Firm—Bacon & Thomas

[57] ABSTRACT

Compounds of the general formula:

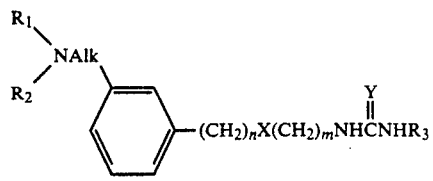

and physiologically acceptable salts, and hydrates, N-oxides and bioprecursors of such compounds and such salts in which $R_1$ and $R_2$, which may be the same or different, represent hydrogen or lower alkyl, cycloalkyl, aralkyl or lower alkenyl groups, or lower alkyl groups interrupted by an oxygen atom or a group

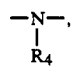

in which $R_4$ represents hydrogen or lower alkyl; or $R_1$ and $R_2$ may, together with the nitrogen atom to which they are attached form a heterocyclic ring which may contain the hetero functions —O— and

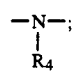

$R_3$ represents hydrogen, lower alkyl, alkenyl or alkoxyalkyl;
X represents —O—, —S— or —CH$_2$— or

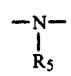

where $R_5$ is hydrogen or lower alkyl;
Y represents =S, =O, =NR$_6$ or =CHR$_7$;
in which $R_6$ represents hydrogen, nitro, cyano, lower alkyl, aryl, arylsulphonyl or lower alkylsulphonyl; $R_7$ represents nitro, lower alkylsulphonyl or arylsulphonyl; m is an integer from 2 to 4 inclusive; n is zero, 1 or 2; and Alk denotes a straight or branched alkylene chain of 1 to 6 carbon atoms. The compounds have therapeutic activity.

19 Claims, No Drawings

PHARMACOLOGICALLY ACTIVE AMINOALKYLPHENYL COMPOUNDS AND THEIR USE

This application is a continuation of application Ser. No. 502,674, filed June 9, 1983, now abandoned; which is a continuation of Ser. No. 200,607, filed Oct. 24, 1980, now abandoned; which is a continuation of Ser. No. 906,619, filed May 16, 1978, now abandoned.

This invention relates to new aminoalkylbenzene derivatives having a selective action on histamine receptors, to processes for the preparation thereof, to pharmaceutical compositions containing them, as well as to their use in therapeutics. It also relates to novel intermediates of use in the processes referred to.

We have found that certain novel aminoalkylbenzene derivatives are selective $H_2$-antagonists that is they show inhibition of the secretion of gastric acid when this is stimulated via histamine $H_2$-receptors (Ash and Schild—Brit. J. Pharmacol. Chemother. 1966 27, 427). Their ability to prevent the secretion of gastric juice when it is stimulated via histamine $H_2$-receptors can be demonstrated in the perfused rat stomach preparation described by Ghosh and Schild—Brit. J. Pharmacol. Chemother. 1958, 13, 54, modified as hereinafter described and in conscious dogs equipped with Heidenhain pouches using the same method as Black et al—Nature 1972 236, 385. The compounds according to the invention do not modify histamine induced contractions of isolated gastrointestinal smooth muscle.

Compounds with histamine $H_2$-blocking activity may be used in the treatment of conditions where there is a hypersecretion of gastric acid e.g. in gastric and peptic ulceration, and in the treatment of allergic conditions where histamine is a known mediator. They may be used, either alone, or in combination with other active ingredients in the treatment of allergic and inflammatory conditions such as urticaria.

The present invention provides compounds of the general formula (I):

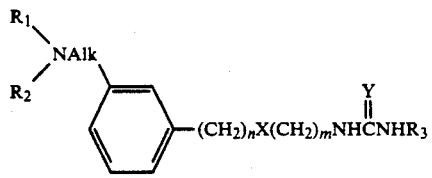

and physiologically acceptable salts, hydrates, N-oxides and bioprecursors thereof in which $R_1$ and $R_2$ which may be the same or different represent hydrogen or lower alkyl, cycloalkyl, aralkyl or lower alkenyl groups or lower alkyl groups interrupted by an oxygen atom or a group

in which $R_4$ represents hydrogen or lower alkyl, or $R_1$ and $R_2$ together with the nitrogen atom to which they are attached form a heterocyclic ring which may contain the hetero functions —O— and

$R_3$ represents hydrogen, lower alkyl, lower alkenyl or alkoxyalkyl;

X is —O—, —S—, —CH$_2$— or

where $R_5$ is hydrogen or lower alkyl; Y represents =S, =O, =NR$_6$ or =CHR$_7$ in which R$_6$ is hydrogen, nitro, cyano, lower alkyl, aryl, arylsulphonyl or lower alkylsulphonyl and R$_7$ is nitro, lower alkylsulphonyl or arylsulphonyl;

m is an integer from 2 to 4 inclusive;

n is zero, 1 or 2; and

Alk denotes a straight or branched alkylene chain of 1 to 6 carbon atoms.

The term 'lower' as applied to 'alkyl' means that the group has a small number of carbon atoms, preferably 1 to 6 carbon atoms, and in particular 1 to 4 carbon atoms and when applied to 'alkenyl' that the group has preferably 3 to 6 carbon atoms. The term 'aryl' preferably means phenyl or substituted phenyl for example phenyl substituted with one or more alkyl, alkoxy or halogen groups.

The compounds of formula (I) can exhibit tautomerism and the formula is intended to cover all tautomers. Where Alk denotes a branched chain alkylene group, optical isomers may exist, and the formula is intended to cover all diastereoisomers and optical enantiomers.

The preferred compounds are those in which $R_1$ and $R_2$ independently represent hydrogen or lower alkyl or together with the nitrogen atom to which they are attached form a 5 or 6-membered heterocyclic ring; Alk represents a straight alkylene chain of 1 to 3 carbon atoms; n is zero or 1; Y is =S, =O, =CHNO$_2$ or =NR$_6$ where R$_6$ is hydrogen, nitro, cyano or alkylsulphonyl; R$_3$ is hydrogen, alkyl or alkoxyalkyl; and m and X have the meanings given above.

In a preferred class of compounds $R_1$ and $R_2$ independently represent hydrogen or methyl or together with the nitrogen atom form a pyrrolidine ring; Alk represents a methylene group; n is zero; Y is =CHNO$_2$ or =NR$_6$ where R$_6$ is nitro, cyano or methylsulphonyl; R$_3$ is hydrogen or methyl; m is 3 and X is oxygen.

Particularly preferred specific compounds are:
N-Methyl-N'-[2-[[3-(N,N-dimethylaminomethyl)-phenyl]methylthio]ethyl]-2-nitro-1,1-ethenediamine
N-Methyl-N'-[2-[[3-(N-methylaminomethyl)phenyl]-methylthio]ethyl]2-nitro-1,1-ethenediamine
N-Methyl-N'-[3-[3-(N,N-dimethylaminomethyl)-phenoxy]propyl]2-nitro-1,1-ethenediamine
N-Methyl-N'-[3-[3-(N-methylaminomethyl)phenoxy]-propyl]2-nitro-1,1-ethenediamine
N-Methyl-N'-[3-[3-(1-pyrrolidinylmethyl)phenoxy]-propyl]2-nitro-1,1-ethenediamine
N-Nitro-N'-[3-[3-(N,N-dimethylaminomethyl)phenoxy]propyl]guanidine
N-Cyano-N'-methyl-N''-[3-[3-(N,N-dimethylaminomethyl)phenoxy]propyl]guanidine
N-Methyl-N'-[3-[3-(N,N-dimethylaminoethyl)phenoxy]propyl]2-nitro-1,1-ethenediamine N-Methanesulphonyl-N'-methyl-N''-[3-[3-(N,N-dimethylaminomethyl)phenoxy]propyl]guanidine.

The compounds of formula (I) form physiologically acceptable salts with inorganic and organic acids. Particularly useful salts include hydrochlorides, hydrobromides and sulphates; acetates, maleates and fumarates. The compounds may also form hydrates.

The compounds according to the invention can be administered orally, topically or parenterally or by suppository, of which the preferred route is the oral route. They may be used in the form of a base or as a physiologically acceptable salt. They will in general be associated with a pharmaceutically acceptable carrier or diluent, to provide a pharmaceutical composition.

The compounds according to the invention can be administered in combination with other active ingredients, e.g. conventional anti-histamines if required. For oral administration the pharmaceutical composition can be most conveniently in the form of capsules or tablets, which may be slow release tablets. The composition may also take the form of a dragee or may be in syrup form. Suitable topical preparations include ointments, lotions, creams, powders and sprays.

A convenient daily dose by the oral route would be of the order of 10 mg to 2 g per day, in the form of dosage units containing from 2 mg to 200 mg per dosage unit.

Parenteral administration may be by injections at intervals or as a continuous infusion. Injection solutions may contain from 1 to 100 mg/ml of active ingredient.

For topical application a spray, ointment, cream or lotion may be used. The compositions may contain an effective amount of the active ingredient, for example of the order of 1½ to 2% by weight of the total composition.

The above compositions may be suitable for either human or veterinary use.

The compounds of formula (I) may be made by reacting a primary amine of the formula (II)

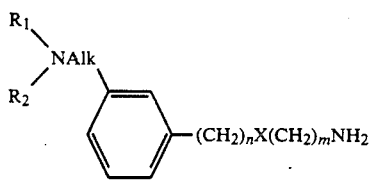
(II)

(in which $R_1$, $R_2$, Alk, n, X and m have the meanings previously defined) with a compound capable of introducing the group

in which $R_3$ and Y have the meanings given herein.

Compounds which are capable of introducing the group

are isocyanates $R_3NCO$, isothiocyanates $R_3NCS$ or compounds of the formula (III):

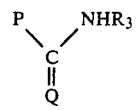
(III)

wherein Q represents a group $=NR_6$ or $=CHR_7$ and P is a leaving group such as halogen, thiomethyl, 3,5-dimethylpyrazolyl or alkoxy, but is preferably thiomethyl.

The reaction with the isocyanate or isothiocyanate may be carried out by allowing the amine (II) and isocyanate or isothiocyanate to stand in a solvent such as acetonitrile. The reaction of the amine (II) with a compound of formula (III) can be carried out by fusing the reactants at an elevated temperature e.g. 100°–120° C. Where Q is $=NR_6$, the reaction between the amine (II) and the compound (III) may also be carried out in a solvent, e.g. acetonitrile or ethanol at elevated temperatures. Where Q is $=CHR_7$, the amine (II) and the compound (III) may be stirred in aqueous solution at room temperature.

Where $R_3$ represents hydrogen, alkali metal cyanates and thiocyanates may be used, the reaction being effected at elevated temperature. Alternatively, organic isocyanates and isothiocyanates may be used e.g. ethylcarbonisothiocyanatidate, followed by basic hydrolysis.

In an alternative process, the amine of formula (II) is reacted with a compound of formula (IV):

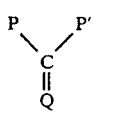
(IV)

where P and Q are as defined above and P' may have the same meanings as P or may, when Q represents $=CHNO_2$, be a group

wherein A represents a lower alkyl group e.g. methyl.

The resulting compound of formula (V)

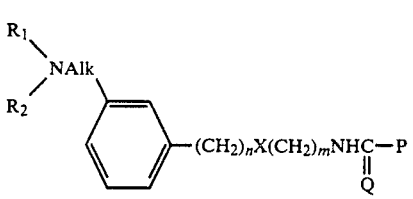
(V)

may then be reacted with an amine $R_3NH_2$ to give a compound of formula (I). Both steps of the reaction may be effected in a solvent e.g. ethanol or acetonitrile at a temperature from ambient to reflux.

Compounds of the invention in which n is 1, X is sulphur and the other groups have the meanings given except that when $R_1$ and $R_2$ are both hydrogen, Y is other than $=CHR_7$ may also be prepared from compounds of formulae (VI) or (VII) using a thiol of formula (VIII):

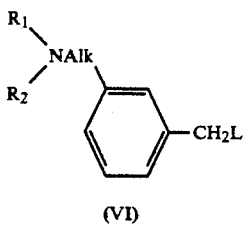

(VI)

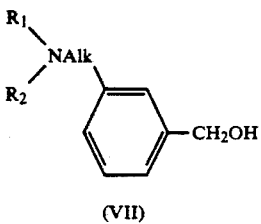

(VII)

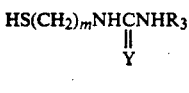

(VIII)

In the above formula (VI) L represents a leaving group e.g. halogen (e.g. bromine) or an acyloxy (e.g. acetoxy) group. Where one is producing compounds in which $R_1$ and $R_2$ are hydrogen, the amino group $NR_1R_2$ is protected in compounds of formula (VI) and (VII) as, in the case of a primary amine, for example, a phthalimido group, in which case the protecting group may be cleaved at an appropriate stage in the reaction using a primary amine or a hydrazine e.g. methylamine or hydrazine hydrate.

The reaction between a thiol (VIII) and a compound of formula (VI) is preferably carried out in the presence of a strong base e.g. sodium hydride at room temperature in an organic solvent e.g. dimethylformamide. The reaction between a thiol (VIII) and a compound of formula (VII) is preferably carried out at 0° C. in a mineral acid e.g. concentrated hydrochloric acid. The starting materials of formula (VI) may be prepared from alcohols of formula (VII) by conventional means.

Another process for preparing compounds according to the invention where Y is sulphur and $R_1$ and $R_2$ are other than hydrogen involves treatment of the amine (II) with carbon disulphide followed by reaction with a chloroformate ester e.g. ethyl chloroformate to give an isothiocyanate of formula (IX)

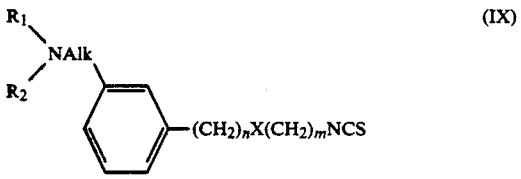

When the resulting compound of formula (IX) is reacted with an amine $R_3NH_2$, preferably in a solvent such as acetonitrile, the product is a compound of formula (I) wherein Y is sulphur and $R_1$ and $R_2$ are other than hydrogen.

Compounds of formula (I) where Y is a group =NCN may be prepared from compounds of formula (I) wherein Y is sulphur by heating the latter compounds with a heavy metal cyanamide such as that of silver, lead, cadmium or mercury, preferably in aqueous solution.

When the groups $R_1$ and $R_2$ in compounds of formula (I) in which Y is other than =S are hydrogen they may be converted into alkyl or aralkyl groups by reaction with, for example, an alkyl or aralkyl halide. If compounds in which $R_1$ and/or $R_2$ are methyl groups are desired an alternative would be to use formic acid and formaldehyde as in the Eschweiler-Clarke reaction.

In the above discussion of the processes available for the production of the compounds according to the invention, reference has been made to primary amines of formula (II). These amines are novel compounds and the invention includes such compounds and acid addition salts thereof with inorganic and organic acids. These intermediates may be made by a number of processes which are described below.

Amines of formula (II) wherein X is oxygen or sulphur may be prepared from compounds of formula (X)

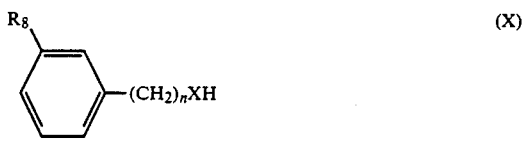

wherein X is oxygen or sulphur and $R_8$ is the group $R_1R_2NAlk$ or a group convertible thereto as appropriate, as herein described and n has the meanings given above by reaction in the presence of a base e.g. sodium hydride with compounds of formula (XI)

in which L' has the meanings given for L or in addition may be a sulphonyloxy group e.g. mesyloxy or tosyloxy, m is as defined above and W is a group —$NH_2$ or a group convertible thereto. Where W is a protected amino group e.g. phthalimido, the protecting group may subsequently be cleaved by means described above.

Groups convertible into the group $R_1R_2NAlk$ include aldehyde, nitrile, carboxylic acid or amide groups and phthalimido groups. For example, the group —CHO may be converted by reductive amination using an amine $R_1R_2NH$. Similarly, a carboxylic acid group may be converted into the corresponding acid halide or ester which may then be reacted with an amine $R_1R_2NH$, followed by reduction of the amide so formed with, for example, lithium aluminium hydride to give a group $R_1R_2NCH_2$—.

Amines of formula (II) wherein n is 1 and X is oxygen or sulphur may be prepared by reaction of a compound of formula (VI) or (VII) with a compound capable of introducing the group —$X(CH_2)_mNH_2$ wherein X is oxygen or sulphur and m has the meanings given herein. When a compound of formula (VI) is used, the presence of a base is desirable. When a compound of formula (VII) is used, the reaction is done under acidic conditions.

Amines of formula (II) in which n is 1, m is 2 and X is oxygen or sulphur can be obtained by treating a compound of formula (X) in which n is 1 and X is oxygen or sulphur with ethylene imine.

Amines of formula (II) in which n is zero, m is 3 and X is oxygen may be obtained from the corresponding nitrile of formula (XII)

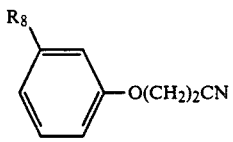 (XII)

by catalytic hydrogenation, for example using rhodium on aluminium oxide.

A compound of formula (XII) may be prepared from a phenol of formula (XIII)

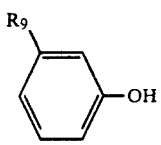 (XIII)

where $R_9$ is a group convertible to $R_1R_2NAlk$ e.g. an aldehyde, by reaction with acrylonitrile in the presence of a base e.g. methanolic benzyl trimethylammonium hydroxide.

Amines of formula (II) wherein X is a methylene group may be prepared from compounds of formula (XIV)

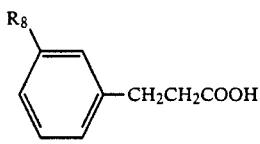 (XIV)

in which $R_8$ is for example a group $R_1R_2NAlk$ or a carboxamide or nitrile group, by standard methods. For example, reaction of the derived acid chloride or ester of a compound of formula (XIV) with ammonia, followed by reduction of the resulting amide yields an amine of formula (II) in which X is $-CH_2-$, n is zero and m is 2.

Alternatively reduction of a compound of formula (XIV) wherein $R_8$ is, for example, a group $R_1R_2NAlk$ or a carboxamide or nitrile group with, for example, lithium aluminium hydride would yield an alcohol of formula (XV)

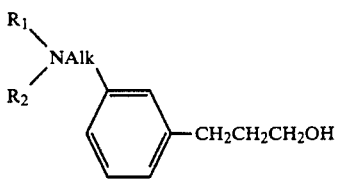 (XV)

which may be converted into a compound of formula (XVI)

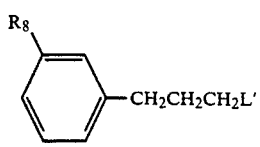 (XVI)

wherein $R_8$ is $R_1R_2NAlk$ and $L'$ has the meanings given above.

Compounds of formula (XVI) may then be reacted with ammonia to give an amine of formula (II) in which X is $-CH_2-$, n is zero and m is 2. Reaction of a compound of formula (XVI) with an alkali metal cyanide e.g. potassium cyanide would yield a compound of formula (XVII)

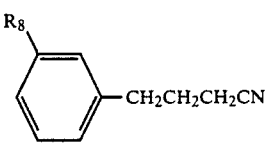 (XVII)

which may then be reduced with, for example, lithium aluminium hydride to yield an amine of formula (II) in which X is $-CH_2-$ and the sum of m+n is 3. Alternatively, a compound of formula (XVII) may be hydrolysed to a compound of formula (XVIII)

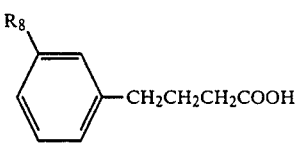 (XVIII)

which may then be converted into an amine of formula (II) wherein X is $-CH_2-$ and the sum of m+n is 3 for example by reaction of ammonia with the derived acid chloride, followed by reduction as described above.

Amines of formula (II) in which n is zero and X is a group $-NH-$ may be prepared from starting materials of formula (XIX)

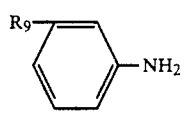 (XIX)

where $R_9$ is a group convertible to a group $R_1R_2NAlk$ e.g.

by reaction with a compound of formula (XI) with subsequent removal of any protecting groups and reduction of the amide function.

The starting materials of formula (XIV) may be obtained for example by catalytic reduction of compounds of formula (XX) with attendant or subsequent modification of the aldehyde function.

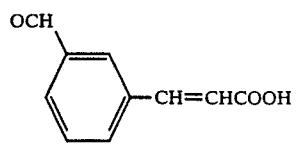 (XX)

For example, where the reduction is performed in the presence of an amine, $R_1R_2NH$, the aldehyde may be converted into a group $R_1R_2NCH_2$.

In the reactions described above for preparing amines of formula (II) it is usually preferable to use intermediates containing the desired $R_1R_2NAlk$ group, or a protected form thereof e.g. phthalimido. However, one may take intermediates containing a group convertible to said $R_1R_2NAlk$ group and convert such a group into $R_1R_2NAlk$ at any suitable stage in the overall preparation.

Where $R_1$ and $R_2$ are both hydrogen in intermediates to amines of formula (II), the primary amino function may be protected, for example as a phthalimido group in any of the above reaction, the protecting group being cleaved at a suitable stage by means described herein.

Where $R_1$ and/or $R_2$ are hydrogen in intermediates to amines of formula (II), they may be converted where appropriate into alkyl or aralkyl groups using, for example an alkyl or aralkyl halide. Where $R_1$ and/or $R_2$ are methyl, a reaction with formaldehyde and formic acid in the Eschweiler-Clarke procedure may be suitable.

In order that the invention may be more fully understood the following exemplification is provided by way of illustration only. Preparations 1 to 6 describe the preparation of starting materials, Examples A to F the preparation of intermediates of formula (II), and Examples 1 to 8 the preparation of compounds of formula (V) and of formula (I). In this exemplification:
i) TLC measurements were carried out on silica gel plates of thickness 0.25 mm mounted on a plastic support.
ii) NMR data is recorded in $\tau$ values.
iii) Distillation pressures were measured in millimeters of mercury.

PREPARATION 1

3-(1-Pyrrolidinylmethyl)phenol

Sodium borohydride (15.2 g) was added to a solution of 3-hydroxybenzaldehyde (48.8 g) and pyrrolidine (66.4 ml) in ethanol. After 18 hours the ethanol was removed and the residual oil was acidified with hydrochloric acid and washed with ethyl acetate. The aqueous solution was then basified with ammonia and extracted with ethyl acetate. Evaporation of the organic extracts yielded the title compound as an off-white solid (21.4 g), m.p. 100°–102°. TLC Silica; methanol; 0.88 ammonia (80:1)Rf 0.48.

PREPARATION 2

3-(N,N-Dimethylaminomethyl)benzenemethanol (1) (a) 3-(N,N-dimethylaminocarbonyl)benzoic acid, methyl ester A mixture of thionyl chloride (88 g) and benzene-1,3-dicarboxylic acid monomethyl ester (33 g) was heated at 100° for 1.5 hours. The excess thionyl chloride was removed by distillation to leave an oil which was used without further purification. The oil in dioxan was added to a cold solution of aqueous dimethylamine (40%; 56 ml) in dioxan, and stirred at 5° for 1 hour. The reaction mixture was poured into dilute hydrochloric acid and extracted with chloroform. The organic phase was dried and evaporated to give an oil (36 g). TLC silica; ethyl acetate, Rf 0.8. NMR (CDCl$_3$) 1.8 m (2H); 2.2–2.7 m (2H); 6.1 s (3H); 6.95 s (6H).

(1) (b) The above example was repeated using the ester (70 g) and 25% aqueous methylamine (118 ml) to give 3-(N-methylaminocarbonyl)benzoic acid methyl ester (54 g) m.p. 128°–130°. TLC silica; ethyl acetate Rf 0.57.

(2) (a) 3-(N,N-Dimethylaminomethyl)benzenemethanol 3-(N,N-Dimethylamino carbonyl)benzoic acid, methyl ester (36 g) in dry tetrahydrofuran was added to lithium aluminium hydride (16.6 g) in dry tetrahydrofuran. The reaction mixture was heated at 60° for 3 hours, cooled and treated with water. The solvent was removed and the residue treated with dilute hydrochloric acid. The mixture was basified with sodium hydroxide and extracted with chloroform. The organic extracts were dried and distilled to give an oil (16 g) b.p. 95°–100° (0.1 mm). TLC silica/methanol Rf 0.57.

(2) (b) The above example was repeated using 25 g of the ester of (b) above to give 3-(N-methylaminomethyl)benzenemethanol (9.2 g) b.p. 110°–115° (0.02 mm). TLC silica; methanol. RF 0.36.

PREPARATION 3

(a) 2-[3-[3-(N,N-Dimethylaminomethyl)phenoxy]-propyl]-1H-isoindole-1,3(2H)-dione A mixture of 80% sodium hydride (2.2 g) and 3-(N,N-dimethylaminomethyl)phenol (6.95 g) in dry dimethylformamide was stirred at 5° for 2 hr. N-(3-Bromopropyl)phthalimide (12.2 g) was then added and after 16 hours the reaction was treated with water and extracted with ethyl acetate. Evaporation of the dried organic extracts gave the title compound as a yellow oil (13 g). TLC silica; ethyl acetate; Rf 0.35. m.p. (oxalate salt) 204°–207°.

The following compounds were prepared similarly from the corresponding phenol (A) and appropriate bromoalkylphthalimide (B).

(b) A (14 g)+B (21.5 g) gave 2-[3-[3-(1-pyrrolidinylmethyl)phenoxy]propyl]-1H-isoindole-1,3(2H)-dione (21.4 g). TLC silica; methanol:0.880 ammonia (80:1) Rf 0.46. m.p. (oxalate salt) 167°–9°.

(c) A (5 g)+B (9.3 g) gave 2-[4-[3-(N,N-dimethylaminomethyl)phenoxy]butyl]-1H-isoindole-1,3(2H)-dione (8.7 g). TLC silica; methanol:0.88 ammonia (80;1) Rf 0.56, m.p. (oxalate salt) 169°–70°.

(d) A (5 g)+B (8.1 g) gave 2-[3-[3-(N,N-dimethylaminoethyl)phenoxy]propyl]-1H-isoindole-1,3(2H)-dione (5 g) m.p. 59°–60°. TLC silica; ethyl acetate:isopropanol:water:0.88 ammonia (25:15:8:2) Rf 0.45.

(e) A (2.0 g)+B (3.4 g) gave 2-[4-[3-(N,N-dimethylaminoethyl)phenoxy]butyl]-1H-isoindole-1,3(2H)-dione (2.8 g) m.p. 52°–3°. TLC silica; ethyl acetate:isopropanol:water:0.88 ammonia (25:15:8:2) Rf 0.55.

(f) A (2.2 g)+B (3.2 g) gave 2-[3-[3-(N,N-dimethylaminopropyl)phenoxy]propyl]-1H-isoindole-1,3(2H)-dione (2.5 g) b.p. 250° (0.1 mm). TLC silica; ethyl acetate:isopropanol:water:ammonia (25:15:8:2) Rf 0.5.

(g) A (2.2 g)+B (3.4 g) gave 2-[4-[3-(N,N-dimethylaminopropyl)phenoxy]butyl]-1H-isoindole-1,3(2H)-dione (2.6 g) b.p. 225° (0.04 mm). TLC silica; ethyl acetate:isopropanol:water:0.88 ammonia, Rf 0.5.

PREPARATION 4

(a) 2-[2-[3-(N,N-Dimethylaminomethyl)phenoxy]ethyl]-1H-isoindole-1,3-(2H)-dione 3-(N,N-Dimethylaminomethyl)phenol (5.0 g), 80% sodium hydride (1.2 g) and 2-[2-(4-methylbenzenesulphonyl)ethyl]-1H-isoindole-1,3(2H)-dione (13 g) were heated at 90° in dimethylformamide. After 12 hours the reaction mixture was cooled, poured onto ice-water and extracted with ether. Evaporation of the organic solvent gave the product as a viscous yellow oil (5.2 g). TLC silica; methanol:ethyl acetate (1:1) Rf 0.37. m.p. (oxalate salt) 166°–7°.

The following compounds were similarly prepared from the corresponding phenol (A) and 2-[2-(4-methylbenzenesulphonyl)ethyl]-1H-isoindole-1,3(2H)-dione (C).

(b) A (5 g)+C (11.7 g) gave 2-[2-[3-(N,N-dimethylaminoethyl)phenoxy]ethyl]-1H-isoindole-1,3(2H)-dione (2.4 g) m.p. 84°–5°. TLC silica; ethyl acetate:isopropanol:water:0.88 ammonia, Rf 0.45.

(c) A (2.2 g)+C (4.2 g) gave 2-[2-[3-(N,N-dimethylaminopropyl)phenoxy]ethyl]-1H-isoindole-1,3(2H)-dione (0.5 g). TLC silica; ethyl acetate:isopropanol:water:0.880 ammonia (25:15:8:2) Rf 0.45.

PREPARATION 5

2-[3-[3-(N,N-Dimethylaminomethyl)phenoxy]propyl]-1H-isoindole-1,3(2H)-dione (1)

2-[3-[3-(Formyl)phenoxy]propyl]-1H-isoindole-1,3(2H)-dione

3-Hydroxybenzaldehyde (0.61 g), 3-bromopropylphthalimide (1.31 g) and potassium carbonate were stirred in dimethylformamide for 16 hours at room temperature. The reaction mixture was poured into water to precipitate the title compound (1.37 g) which was filtered off and dried m.p. 102°–4°. TLC silica; methanol:toluene (1:9) Rf 0.65.

(2)

2-[3-[3-(N,N-Dimethylaminomethyl)phenoxy]propyl]-1H-isoindole-1,3(2H)-dione

2-[3-[3-(Formyl)phenoxy]propyl]-1H-isoindole-1,3(2H) dione (132 g) and 33% ethanolic dimethylamine (300 ml) were hydrogenated at room temperature and atmospheric pressure in ethanol over 10% palladium on charcoal. The catalyst was filtered off and the filtrate evaporated to give the title compound as a yellow oil (142 g). TLC silica (ethyl acetate) Rf 0.35, m.p. (oxalate salt) 204°–207°.

PREPARATION 6

2-[3-[[3-(N,N-Dimethylaminomethyl)phenyl]thio]propyl]-1H-isoindole-1,3-(2H)dione (1) Dithio bis-3,3'-N,N-dimethylbenzenecarboxamide Dimethylamine (57 ml) in toluene was added at 5° to 3,3'-dithio(chlorocarbonyl)benzene (46 g) in toluene. After 4 hours water was added and the solution was extracted with ethyl acetate. Evaporation of the extracts gave the product as an orange oil (49 g). NMR (CDCl$_3$) 2.4–2.8 m (8H); 7.05 br (12H).

(2) Dithio bis-3,3'-N,N-dimethylbenzenemethanamine 3,3'-Dithio N,N-dimethylbenzenecarboxamide (48 g) in dry ether was added to lithium aluminium hydride (20 g) in dry ether. The reaction mixture was stirred at room temperature, cooled, treated with water and filtered. The filtrate was extracted with ethyl acetate and the extracts were dried and distilled to give a colourless oil (8.8 g) b.p. 250° (0.1 mm). NMR (CDCl$_3$) 2.5–2.9 m (8H); 6.66 s (4H); 7.8 s (6H).

(3)

2-[3-[[3-(N,N-Dimethylaminomethyl)phenyl]thio]propyl]-1H-isoindole-1,3(2H)dione

80% Sodium hydride (2.3 g) and dithio bis-3,3'-N,N-dimethylbenzenemethanamine (7.8 g) were stirred at room temperature in dry dimethylformamide for 24 hr. N-(3-Bromopropyl) phthalimide (12.6 g) was then added. After 24 hr the reaction was treated with water and extracted with ethyl acetate. The organic extracts were evaporated and the residue purified by column chromatography on silica with ethyl acetate/methanol to give the title compound as a pale orange oil (11.3 g). NMR (CDCl$_3$) 2.0–2.4 m (4H); 2.6–2.9 m (4H); 6.15 t (2H); 6.59 s (2H); 7.02 t (2H); 7.75 s (6H); 7.98 m (2H).

EXAMPLE A 3-(3-Aminopropoxy)-N-methylbenzenemethanamine dioxalate (1) 3-[3-(Formyl)phenoxy]propionitrile A solution of m-hydroxybenzaldehyde (30.5 g) in acrylonitrile (265 ml) and 40% methanolic benzyl trimethylammonium hydroxide (5 ml) was heated under reflux for 20 hr. The mixture was diluted with ether (500 ml) and the solution was washed with 5% sodium hydroxide solution and water. The ethereal solution was dried over magnesium sulphate, filtered and evaporated in vacuo to give a clear colourless oil (32 g). TLC silica, chloroform, Rf 0.4.

(2) 3-(2-Cyanoethoxy)-N-methylbenzenemethanamine, hydrochloride

A solution of 3-[3-(formyl)phenoxy]propionitrile (8.75 g) in a mixture of 33% ethanolic methylamine (50 ml) and ethanol (200 ml) was stirred at room temperature with 5% palladium oxide on charcoal (0.8 g) under hydrogen at 1 atmosphere. After uptake of hydrogen had ceased the mixture was filtered and the residues were washed with ethanol. The ethanolic filtrate and washings were combined, reduced in volume and treated with excess ethereal hydrogen chloride. The precipitated hydrochloride was recrystallised from a mixture of ethanol and ether as colourless plates (7.9 g) m.p. 125°–128°.

Assay Found: C, 58.1; H, 6.5; N, 12.3; C$_{11}$H$_{15}$ClN$_2$O requires: C, 58.3; H, 6.5; N, 12.35%.

(3)

3-(3-Aminopropoxy)-N-methylbenzenemethanamine, dioxalate

A solution of N-methyl-[3-(2-cyanoethoxy)benzenemethanamine hydrochloride (5.39 g) in methanol (50 ml) was eluted through a basic ion-exchange column (Amberlyst A-26) and the eluate was evaporated to give the free base as a colourless oil. The free base was dissolved in ethanol (500 ml) and 0.88 ammonia solution (25 ml) and shaken with 5% rhodium on alumina (2.5 g) at room temperature and under a pressure of 40 psi of hydrogen for 6 hr. The resulting suspension was filtered, evaporated in vacuo and the residue was dissolved in ethanol and treated with excess ethanolic oxalic acid. The precipitated dioxalate salt (6.56 g) was filtered off and dried m.p. 196°–198°. TLC silica; methanol:0.88 ammonia (99:1) Rf 0.1.

EXAMPLE B 3-(3-Aminopropoxy)-N-methylbenzenemethanamine dioxalate

2-[3-[3-(Formyl)phenoxy]propyl]-1H-isoindole-1,3(2H)-dione (8.5 g) was stirred in 33% ethanolic methylamine (300 ml) for 1 hr and then hydrogenated at room temperature and atmospheric pressure in ethanol over 10% palladium on charcoal. The solution was filtered, evaporated to dryness in vacuo, and dissolved in ethanol (50 ml). The ethanolic solution was treated with excess ethanolic oxalic acid and the resulting precipitate was recrystallised from ethanol/water to give the title compound as colourless grains (3.9 g) m.p. 196°–198°. TLC silica; methanol:0.88 ammonia (20:1) Rf 0.1.

EXAMPLE C (a) 3-(3-Aminopropoxy)-N,N-dimethylbenzenemethanamine

2-[3-[3-(N,N-Dimethylaminomethyl)phenoxy]-propyl]-1H-isoindole-1,3(2H)-dione (25 g) was treated with 30% ethanolic methylamine (150 ml). After 24 hr at room temperature ether (100 ml) was added and a solid was filtered off. The filtrate was distilled to give the title compound as a yellow oil (12.3 g) b.p. 102°–112° (0.2 mm). TLC silica; ethyl acetate:isopropanol:water:0.88 ammonia Rf 0.25.

The following compound was similarly prepared from the corresponding phthalimide (C).

(b) C (5.4 g) gave 3-(2-aminoethoxy)-N,N-dimethylbenzenemethanamine (0.45 g). TLC silica; methanol/ammonia (80:1) Rf 0.04. NMR (CDCl$_3$) 2.8–3.1 m (4H): 6.05 t (2H); 6.55 s (2H); 6.98 t (2H); 7.80 s (6H); 8.4 br.s (2H).

EXAMPLE D (a) 3-(3-Aminopropoxy)-N,N-dimethylbenzenemethanamine.

2-[3-[3-(N,N-Dimethylaminomethyl)phenoxy]-propyl]-1H-isoindole-1,3(2H)-dione (90 g) and 30% aqueous methylamine (200 ml) were heated at 80°. After 4 hours the reaction mixture was cooled, basified with 5N sodium hydroxide solution and extracted with toluene. The toluene extract was distilled to give the title compound as a pale yellow oil (43.1 g) b.p. 102°–112° (0.2 mm). TLC silica; ethyl acetate:isopropanol:water:0.88 ammonia (25:15:8:2) Rf 0.25.

The following compounds were similarly prepared from the corresponding phthalimide (C).

(b) C (6.7 g) gave 3-(4-aminobutoxy)-N,N-dimethylbenzenemethanamine (1.2 g). TLC silica; methanol:0.88 ammonia (80:1) Rf 0.24.

(c) C (2.6 g) gave 3-[3-(1-pyrrolidinylmethyl)phenoxy]propylamine isolated as the bis oxalate salt (1.3 g) m.p. 184°–5°. TLC silica; methanol:0.88 ammonia (19:1) Rf 0.3.

EXAMPLE E (a) 3-(3-Aminopropoxy)-N,N-dimethylbenzenemethanamine

2-[3-[3-(N,N-Dimethylaminomethyl)phenoxy]-propyl]-1H-isoindole-1,3(2H)-dione (12.2 g) and hydrazine hydrate (2.1 ml) were heated at reflux in ethanol for 3 hr. The reaction mixture was cooled, filtered and the filtrate was distilled to give the product as a colourless oil (2 g) b.p. 127° (0.6 mm) m.p. (Hydrochloride salt) 212°–215°.

The following compounds were similarly prepared from the corresponding phthalimide (C).

(b) C (2.8 g) gave 3-(2-aminoethoxy)-N,N-dimethylbenzene ethanamine (1.7 g) b.p. 135° (0.03 mm). TLC silica; ethyl acetate:isopropanol:water:0.88 ammonia (25:15:8:2) Rf 0.3.

(c) C (4.2 g) gave 3-(3-aminopropoxy)-N,N-dimethylbenzene ethanamine (2 g) b.p. 95° (0.03 mm). TLC silica; ethyl acetate:isopropanol:water:0.88 ammonia (25:15:8:2) Rf 0.3.

(d) C (2.5 g) gave 3-(4-aminobutoxy)-N,N-dimethylbenzene ethanamine (0.9 g) b.p. 150° (0.04 mm) TLC silica, ethyl acetate:isopropanol:water:0.88 ammonia Rf 0.3.

(e) C (0.5 g) gave 3-(2-aminoethoxy)-N,N-dimethylbenzene propanamine (0.26 g) b.p. 130° (0.03 mm). TLC silica; ethyl acetate:water:isopropanol:0.88 ammonia (25:8:15:2) Rf 0.45.

(f) C (2 g) gave 3-(3-aminopropoxy)-N,N-dimethylbenzene propanamine (0.95 g) b.p. 160° (0.04 mm) TLC silica; ethyl acetate:water:isopropanol:0.88 ammonia (25:8:15:2) Rf 0.3.

(g) C (2 g) gave 3-(4-aminobutoxy)-N,N-dimethylbenzene propanamine (1.05 g) b.p. 130° (0.04 mm). TLC silica; ethyl acetate:water:isopropanol:0.88 ammonia (25:8:15:2) Rf 0.25.

(h) C (11.3 g), gave 3-[(3-aminopropyl)thio]-N,N-dimethylbenzene methanamine (2.3 g) b.p. 142° (0.1 mm) NMR (CDCl$_3$) 2.5–3 m (4H); 6.6 s (2H); 6.99 t (3H) 7.17 t (2H); 7.76 s (6H); 8.22 m (2H); 8.58 brs (2H).

EXAMPLE F (a) 2-[[3-(N,N-Dimethylaminomethyl)phenyl]methylthio]ethanamine.

3-(N,N-Dimethylaminomethyl)benzenemethanol (17.4 g) and cysteamine hydrochloride (12 g), in concentrated hydrochloric acid were heated at 100° for 4 hr. The cooled reaction mixture was treated with solid sodium carbonate and extracted with ether. The organic extracts were distilled to give the product as an oil (21.5 g) b.p. 154°–158° (1.5 mm). m.p. (hydrochloride salt) 180°–182°. TLC silica; ethyl acetate:isopropanol:water:0.88 ammonia (25:15:8:2) Rf 0.37.

(b) From 3-(N-methylaminomethyl)benzene methanol (10.1 g) and cysteamine hydrochloride (7.7 g) was similarly prepared 2-[[3-(N-methylaminomethyl)-phenyl]methylthio]ethanamine (6.5 g) b.p. 140°–145° (0.01 mm). TLC silica; ethyl acetate:isopropanol:water:0.88 ammonia Rf 0.28.

EXAMPLE G 3-(N,N-Dimethylaminomethyl)benzenebutanamine 3-(N,N-Dimethylaminomethyl)benzenepropanoic acid, ethyl ester 3-Formyl cinnamic acid (5.5 g) was heated at 60° in 30% ethanolic dimethylamine (45 ml) for 30 min and then stirred at room temperature with 10% palladium oxide on charcoal (1.5 g) under hydrogen at 1 atmosphere. After uptake of hydrogen had ceased, the mixture was filtered and the filtrate evaporated. The residue was heated under reflux in ethanol and concentrated sulphuric acid for 4 hr. The solution was neutralised with sodium carbonate and distilled to give the product as a colourless liquid (4.2 g) b.p. 130° (0.05 mm).

TLC (silica; ethyl acetate:isopropanol:water:0.88 ammonia (25:15:8:2) Rf 0.75.

3-(N,N-Dimethylaminomethyl)benzenepropanol 3-(N,N-Dimethylaminomethyl)benzenepropanoic acid, ethyl ester (0.5 g) and lithium aluminium hydride (0.2 g) were stirred at room temperature in dry tetrahydrofuran for 2 hr, treated with water and filtered. The filtrate was evaporated to give the product as a colourless liquid (0.34 g).

TLC silica; ethyl acetate:isopropanol:water:0.88 ammonia (25:15:8:2) Rf 0.7. NMR (CDCl$_3$) 2.81 m (4H);

6.33 tr (2H); 6.59 s (2H); 7.28 m (2H); 7.75 s (7H); 7.7-8.4 m (2H).

3-(N,N-Dimethylaminomethyl)benzenebutanenitrile 3-(N,N-Dimethylaminomethyl)benzenepropanol (0.9 g) and p-toluene sulphonyl chloride (0.9 g) were stirred in pyridine for 2 hr. The solvent was evaporated and the residue treated with potassium cyanide (0.7 g) in dimethylformamide at 45° for 16 hr. Water was added and the mixture extracted with ethyl acetate. The extract was distilled to give the product as a colourless liquid (0.3 g) b.p. 110° (0.02 mm).

TLC silica; ethyl acetate:isopropanol:water:0.88 ammonia (25:15:8:2) Rf 0.75.

3-(N,N-Dimethylaminomethyl)benzenebutanamine 3-(N,N-Dimethylaminomethyl)benzenebutanenitrile (0.9 g) and lithium aluminium hydride (0.35 g) in tetrahydrofuran were stirred at room temperature for 2 hr. Water was added and the suspension was filtered. The filtrate was evaporated to give the product as a colourless oil (0.8 g).

TLC silica; ethyl acetate:isopropanol:water:0.88 ammonia (25:15:8:2) Rf 0.1 m.p. (oxalate salt) 125°-7°.

EXAMPLE 1

(a) N-Methyl-N'-[3-[3-(N,N-dimethylaminomethyl)phenoxy]propyl]-2-nitro-1,1-ethenediamine.

A mixture of 3-(3-aminopropoxy)-N,N-dimethylbenzenemethanamine (1 g) and N-methyl-2-nitroimidothioic acid methyl ester (0.78 g) in water (4 ml) was stirred at room temperature for 4 hr. The resultant solution was acidified using glacial acetic acid, then washed with ethyl acetate. The acidic solution was basified with sodium carbonate and extracted with ethyl acetate. The extract was dried over magnesium sulphate, filtered and evaporated to an oil which crystallised from ethereal solution to give the title compound as a white solid (0.6 g), m.p. 81°-3°. TLC silica; ethyl acetate:isopropanol:water:0.88 ammonia (25:15:8:2) Rf 0.6.

The following compounds were similarly prepared from the corresponding diamine and N-methyl-2-nitroimidothioic acid methyl ester (D).

(b) Diamine (2 g) and D (1.4 g) gave N-methyl-N'-[2-[[3-(N-methylaminomethyl)phenyl]methylthio]ethyl]-2-nitro-1,1-ethenediamine (0.8 g). TLC silica; methanol:ammonia (50:1) Rf 0.3, m.p. (fumarate salt) 163°-5°.

(c) Diamine (1 g)+D (0.73 g) gave N-methyl-N'-[3-[[3-(N,N-dimethylaminomethyl)phenyl]thio]propyl]-2-nitro-1,1-ethenediamine (0.25 g) NMR (CDCl₃)-0.5–0.5 brm (1H); 2.5-3 m (4H); 3.4 s (1H); 6.2-6.8 m (4H); 6.8-7.4 m (5H); 7.72 s (6H); 8.02 m (2H).

(d) Diamine (2.5 g)+D (1.8 g) gave N-methyl-N'-[3-[3-(N-methylaminomethyl)phenoxy]propyl]-2-nitro-1,1-ethenediamine (0.35 g). TLC silica; methanol:0.88 ammonia (20:1) Rf 0.35. NMR (CDCl₃) 2.68 m (2H); 2.9-3.4 m (3H); 5.9 t (2H); 6.29 s (2H); 6.53 t (2H); 7.12 br.s (3H); 7.58 s (3H); 7.62-8.2 m (2H).

(e) Diamine (0.45 g)+D (0.24 g) gave N-methyl-N'-[3-[3-(1-pyrrolidinylmethyl)phenoxy]propyl]-2-nitro-1,1-ethenediamine (0.35 g). TLC silica; methanol:0.88 ammonia (80:1) Rf 0.35. NMR (CDCl₃) 2.8 m (1H); 2.9-3.5 m (4H); 5.90 t (2H); 6.4 s (2H); 6.50 m (2H); 7.1 br (4H); 7.5-8.3 m (7H).

(f) Diamine (0.8 g)+D (0.78 g) gave N-methyl-N'-[2-[3-(N,N-dimethylaminomethyl)phenoxy]ethyl]-2-nitro-1,1-ethenediamine (0.55 g) m.p. 130°-1°. TLC silica; methanol:0.88 ammonia (80:1) Rf 0.3.

(g) Diamine (0.7 g)+D (0.52 g) gave N-methyl-N'-[4-[3-(N,N-dimethylaminomethyl)phenoxy]butyl]-2-nitro-1,1-ethenediamine (0.38 g) TLC silica; methanol:0.88 ammonia (80:1) Rf 0.34. NMR (CDCl₃) 0.3 br (1H); 2.82 t (1H); 3.0-3.5 m (5H); 6.08 br (2H); 6.67 m (4H); 7.15 br (3H); 7.81 s (6H); 8.2 br (4H).

(h) Diamine (0.6 g)+D (0.46 g) gave N-methyl-N'-[3-[3-(N,N-dimethylaminoethyl)phenoxy]propyl]-2-nitro-1,1-ethenediamine (0.58 g) m.p. 93°-4°. TLC silica; ethyl acetate:isopropanol:water:0.88 ammonia (25:15:8:2) Rf 0.45.

(i) Diamine (0.5 g)+D (0.36 g) gave N-methyl-N'-[4-[3-(N,N-dimethylaminoethyl)phenoxy]butyl]-2-nitro-1,1-ethenediamine (0.12 g) m.p. 59°-63°. TLC silica; ethyl acetate:isopropanol:water:0.88 ammonia (25:15:8:2) Rf 0.4.

(j) Diamine (0.26 g) and D (0.22 g) gave N-methyl-N'-[2-[3-(N,N-dimethylaminopropyl)phenoxy]ethyl]-2nitro-1,1-ethene diamine (0.2 g) m.p. 82°-83.5°. TLC silica; ethyl acetate:water:isopropanol:0.88 ammonia (25:8:15:2) Rf 0.4.

(k) Diamine (0.2 g)+D (0.15 g) gave N-methyl-N'-[3-[3-(N,N-dimethylaminopropyl)phenoxy]propyl]-2-nitro-1,1-ethenediamine (0.14 g) m.p. 59.5°-61°. TLC silica; ethyl acetate:water:isopropanol:0.88 ammonia (25:8:15:2) Rf 0.35.

(l) Diamine (0.5 g)+D (0.36 g) gave N-methyl-N'-[4-[3-(N,N-dimethylaminopropyl)phenoxy]butyl]-2-nitro-1,1-ethenediamine (0.45 g) m.p. 79°-80.5°. TLC silica; ethyl acetate:water:isopropanol:0.88 ammonia (25:8:15:2) Rf 0.5.

(m) Diamine (0.7 g)+D (0.44 g) gave N-methyl-N'-[4-[3-(N,N-dimethylaminomethyl)phenyl]butyl]-2-nitro-1,1-ethenediamine (0.4 g) m.p. (dihydrochloride) 137°-9°. TLC silica; ethyl acetate:isopropanol:water:0.88 ammonia (25:15:8:2) Rf 0.5.

EXAMPLE 2

N-Nitro-N'-[3-[3-(N,N-dimethylaminomethyl)phenoxy]propyl]guanidine

N-nitrocarbamimidothioic acid methylester (0.77 g) and 3-(3-aminopropoxy)-N,N-dimethylbenzenemethanamine (1.0 g) were heated in ethanol at 40° for 20 mins. The solution was cooled to precipitate the title compound which was filtered off and recrystallised from ethyl acetate as a white solid (0.44 g) m.p. 114°-115°. TLC silica; methanol:0.88 ammonia (80:1) Rf 0.48.

EXAMPLE 3

N-[3-[3-(N,N-Dimethylaminomethyl)phenoxy]propyl]guanidine dinitrate 3-(3-Aminopropoxy)-N,N-dimethylbenzenemethanamine (2 g) and 3,5-dimethylpyrazole-1-carboxamidine nitrate (2.1 g) were heated at reflux in ethanol for 16 hr. The solvent was removed and the residue was washed with boiling ethyl acetate before it was crystallised from ethanol to give the title compound as a white solid (1 g) m.p. 123°-4°.

TLC silica; ethyl acetate:isopropanol:water:0.88 ammonia (25:15:8:2) Rf 0.34.

EXAMPLE 4

(a) N-Cyano-N'-methyl-N''-[3-[3-(N,N-dimethylaminomethyl)phenoxy]propyl]guanidine.

N-Cyano-N'-methylcarbamimidothioic acid methyl ester (0.8 g) and 3-[3-aminopropoxy]-N,N-dimethylbenzenemethanamine (1.0 g) were heated together at 100° for 12 hours. The melt was cooled, dissolved in methanol, filtered and the filtrate was evaporated. The residue was purified by column chromatography on silica with methanol to give the title compound as a clear yellow oil (0.54 g). TLC silica; methanol:0.88 ammonia (80:1) Rf 0.51.

Assay Found: C, 62.54; H, 8.31; N, 23.93; $C_{15}H_{23}N_5O$ requires: C, 62.28; H, 7.96; N, 24.22%.

Similarly prepared from the corresponding amine (5 g) and N-cyano-N'-methylcarbamimidothioic acid methyl ester (2.8 g) was (b) N-cyano-N'-methyl-N''-[2-[[3-(N,N-dimethylaminomethyl)phenyl]methylthio]ethyl]guanidine (2.3 g). TLC silica; methanol, Rf 0.47. NMR (CDCl₃) 2.5-3 m (4H); 6.25 s (2H); 6.5-6.9 m (4H): 7.18 d (3H); 7-7.5 m (2H); 7.73 s (6H).

EXAMPLE 5

N-Methyl-N'-[3-[3-(N,N-dimethylaminomethyl)-phenoxy]propyl]urea

Methyl isocyanate (0.27 ml) and 3-(3-aminopropoxy)-N,N-dimethylbenzenemethanamine (0.97 g) were stirred at room temperature in acetonitrile for 2 hours. The title compound was filtered off, washed with acetonitrile and recrystallised from ethyl acetate as colourless prisms (0.49 g) m.p. 79.5°–80°. TLC silica; methanol:0.88 ammonia (80:1) Rf 0.45.

EXAMPLE 6

N-Methyl-N'-[2-[[3-(N,N-dimethylaminomethyl)-phenyl]methylthio]ethyl]thiourea

2-[[3-(N,N-Dimethylaminomethyl)phenyl]methylthio]ethanamine (5 g) and methyl isothiocyanate (1.62 g) were stirred at room temperature in acetonitrile for 18 hours. The solvent was removed and the residue was column chromatographed on silica using a mixture of ethyl acetate and methanol as eluent to give the title compound as a pale yellow oil. TLC silica; ethyl acetate:isopropanol:water:0.88 ammonia (25:15:8:2) Rf 0.61.

EXAMPLE 7

N-Methyl-N'-[2-[[3-(N,N-dimethylaminomethyl)-phenyl]methylthio]ethyl]-2-nitro-1,1-ethenediamine 2-[[3-(N,N-Dimethylaminomethyl)phenyl]methylthio]ethanamine (3 g) and 1-nitro-2,2-bis(methylthio)ethylene (2.2 g) were heated under reflux in acetonitrile for 7 hours. The solvent was removed and the residual oil used without further purification. The oil was treated with ethanolic methylamine (33%, 34 ml) and heated under reflux for 3 hours. The solvent was removed and the residual oil was purified by column chromatography on silica with methanol. The resultant orange oil was triturated with ether to give the title compound as a white crystalline solid (0.23 g) m.p. 62°-4°. TLC silica; ethyl acetate:isopropanol:water:0.88 ammonia (25:15:8:2) Rf 0.36.

EXAMPLE 8

(a) N-[3-[3-(N,N-Dimethylaminomethyl)phenoxy]-propyl]-N'-(2-methoxyethyl)-2-nitro-1,1-ethenediamine hydrochloride (1) N-[3-[3-(N,N-Dimethylaminomethyl)phenoxy]-propyl]-2-nitroimidothioic acid methyl ester 3-(3-Aminopropoxy)-N,N-dimethylbenzenemethanamine (10 g) and 1-nitro-2,2-bis(methylthio)ethylene (16 g) were heated under reflux in tetrahydrofuran for 19 hours. Oxalic acid dihydrate (1.3 g) was added and the resulting precipitate was discarded. The solvent was removed to leave the title compound as a crystalline solid (10 g) m.p. 59°–63°.

Assay Found: C, 54.95; H, 7.15; N, 12.95; $C_{15}H_{23}N_3O_3S$ requires: C, 55.35; H, 7.05; N, 12.9%.

(2) N-[3-[3-(N,N-Dimethylaminomethyl)phenoxy]-propyl]-N'-(2-methoxyethyl)-2-nitro-1,1-ethenediamine hydrochloride A mixture of N-[3-[3-(N,N-dimethylaminomethyl)-phenoxy]propyl]-2-nitroimidothioic acid methyl ester (0.8 g) and 2-methoxyethylamine (0.2 g) was stirred at room temperature in ethanol for 24 hours. The solvent was removed to leave an orange oil which was treated with ethanolic hydrogen chloride to give the title compound (0.4 g) m.p. 109°–112°.

Assay Found: C, 52.1; H, 7.7; N, 14.0; $C_{17}H_{28}N_4O_4$ requires: C, 52.5; H, 7.45; N, 14.4%.

The following compounds were similarly prepared from the ester and the corresponding amine:

(2) (b) Ester (0.8 g) and 70% aqueous ethylamine (3 ml) gave N-ethyl-N'-[3-[3-(N,N-dimethylaminomethyl)phenoxy]propyl]-2-nitro-1,1-ethenediamine hydrochloride (0.69 g) m.p. 144°–145°. TLC silica; ethyl acetate:isopropanol:water:0.88 ammonia (25:15:8:2) Rf 0.55.

(2) (c) Ester (0.8 g) and 0.88 ammonia (0.5 ml) gave N-[3-[3-(N,N-dimethylaminomethyl)phenoxy]propyl]-2-nitro-1,1-ethenediamine hydrochloride (0.6 g) m.p. 100°–102°. TLC silica; ethyl acetate:isopropanol:water:0.88 ammonia (25:15:8:2) Rf 0.65.

EXAMPLE 9

N-Methanesulphonyl-N'-methyl-N''-[3-[3-(N,N-dimethylaminomethyl)phenoxy]propyl]guanidine N-Methanesulphonylcarbonimidodithioic acid dimethyl ester (3 g) and 3-[3-aminopropoxy]-N,N-dimethylbenzenemethanamine (2.5 g) were heated at reflux in ethanol for 4 hours. Methylamine was then added and the reflux continued for 1½ hours. The solvent was removed and the residue was purified by column chromatography on silica with methanol to yield the title compound as a yellow gum (1.9 g). TLC methanol:0.88 ammonia (80:1) Rf 0.65. NMR (CDCl₃) 2.85 m (1H); 2.9–3.3 m (3H); 3.0–4.3 brs (2H); 5.90 t (2H); 6.5 q (2H); 6.6 s (2H); 7.1 s (6H); 7.75 s (6H); 7.9 m (2H).

EXAMPLE 10

Pharmaceutical Compositions

| (a) Oral Tablets 50 mg | for 10,000 tablets |
|---|---|
| Active ingredient | 500 g |
| Anhydrous lactose U.S.P. | 2.17 kg |
| Sta-Rx 1500 Starch* | 300 g |
| Magnesium Stearate B.P. | 30 g |

*A form of directly compressible starch, supplied by A. E. Staley Mfg. Co. (London) Limited, Orpington, Kent.

The drug is sieved through a 250 μm sieve and then the four powders are intimately mixed in a blender and compressed between 8.5 mm diameter punches in a tabletting machine.

| (b) Injection for Intravenous administration (50 mg in 2 ml) | | % w/w |
|---|---|---|
| Active ingredient | | 2.5 |
| Water for Injections BP | to | 100.0 |
| Dilute Hydrochloric acid BP | to | pH 5.0 |

The active ingredient is dissolved with mixing in the Water for Injection, adding the acid slowly until the pH is 5.0. The solution is sparged with nitrogen and is then clarified by filtration through a membrane filter of pore size 1.35 μm. It is packed into 2 ml glass ampoules (2.2 ml in each) and each ampoule sealed under an atmosphere of nitrogen. The ampoules are sterilised in an autoclave at 121° for thirty minutes.

| (c) Oral Sustained Release Tablets 150 mg | for 10,000 tablets |
|---|---|
| Active ingredient | 1.50 kg |
| Cutina HR** | 0.40 kg |
| Anhydrous lactose U.S.P. | 2.060 kg |
| Magnesium Stearate BP | 40 g |

**Cutina HR is a grade of microfine hydrogenated castor oil supplied by Sipon Products Limited, London.

The active ingredient, anhydrous lactose and most of the Cutina HR are intimately mixed and then the mixture is moistened by mixing with a 10% solution of the remainder of the Cutina HR in Industrial Methylated Spirit OP 74. The moistened mass is granulated through a 1.2 mm aperture sieve and dried at 50° C. in a fluidised bed dryer. The granules are then passed through a 0.85 mm aperture sieve, blended with the magnesium stearate and compressed to a hardness of at least 10 kg (Schleuniger tester) on a tabletting machine with 12.5 mm diameter punches.

| (d) Oral Capsules 50 mg | for 10,000 capsules |
|---|---|
| Active ingredient | 500 g |
| Sta-Rx 1500* | 1700 g |
| Magnesium Stearate BP | 20 mg |

*A form of directly compressible starch, supplied by A. E. Staley Mfg. Co. (London) Limited, Orpington, Kent.

The drug is sieved through a 250 μm mesh sieve and is then blended with the other powders. The powder is filled into No. 3 size hard gelatin capsules on a suitable filling machine.

The compounds of the formula (I) have been found to be inhibitors of gastric acid secretion induced by histamine. This has been shown in rats using a modification of the procedure described by M. N. Ghosh and H. O. Schild in the British Journal of Pharmacology 1958, Vol. 13, page 54.

Female rats weighing about 150 g are starved overnight and provided with 8% sucrose in normal saline instead of drinking water.

The rats are anaesthetized by a single intraperitoneal injection of 25% w/v urethane solution (0.5 ml/100 g) and the trachea and jugular veins cannulated.

A mid-line incision in the abdomen wall is made to expose the stomach which is separated from the liver and spleen by cutting the connective tissue. A small opening is made in the fundic region of the stomach and the stomach washed with a 5% dextrose solution. The oesophagus is cannulated with rubber tubing and the oesophagus and vagi are then cut above the cannula.

A small opening is then made in the pyloric region of the stomach. A large perspex cannula is then placed in the stomach via the opening in the fundic region in such a manner that the inlet end of the cannula passes out of the stomach through the opening in the pyloric region. The cannula is of such a shape so as to reduce the effective volume of the stomach and to provide a turbulent flow of the perfusion fluid over the mucosal surface. A drainage cannula is then inserted through the opening in the fundic region of the stomach. Both cannulae are tied in place by ligatures around the stomach, positioned to avoid the main blood vessels. Stab wounds are made in the body wall and the cannulae passed through. The stomach is perfused through the oesophageal and pyloric cannulae with 5% dextrose solution at 39° C. at a rate of 1.5 ml/min. for each cannula. The effluent is passed over a micro-flow pH electrode and recorded via a pH meter and flat bed recorder.

The basal output of acid secretion from the stomach is monitored by measurement of the pH of the perfusion effluent and then increased acid secretion is induced by a continuous intravenous infusion of a sub-maximal dose of histamine; this produces a stable plateau of acid secretion and the pH of the perfusion effluent is determined when this condition is obtained.

The test compound is then administered to the rat by an intravenous injection and the change in 'gastric' acid secretion is monitored by measuring the change in the pH of the perfusion effluent.

From the change in pH of the perfusion effluent, the difference in acid secretion between basal output and the histamine stimulated plateau level is calculated as hydrogen ion concentration in mole/l. The reduction of acid secretion caused by the administration of the test compound is also calculated as the change in hydrogen ion concentration in mole/l from the difference in the pH of the perfusion effluent. The percentage reduction in acid secretion caused by the administration of the test compound may then be calculated from the two figures obtained.

I claim:

1. A compound of the formula:

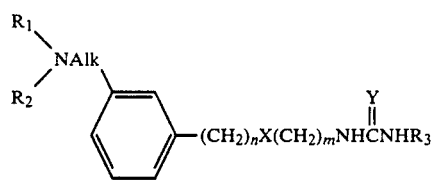

and physiologically acceptable salts, and hydrates of such compounds in which $R_1$ and $R_2$, which may be the same or different, represent hydrogen or $C_{1-6}$ alkyl; or $R_1$ and $R_2$ may, together with the nitrogen atom to which they are attached, form a 5- or 6-membered heterocyclic ring;

$R_3$ represent hydrogen, $C_{1-6}$ alkyl or $C_{1-6}$ alkoxy $C_{1-6}$ alkyl;

X represents —O—;

Y represents =S, =O, =CHNO$_2$ or =NR$_6$, in which $R_6$ represents hydrogen, nitro, cyano or $C_{1-6}$ alkylsulphonyl;

m is an integer from 2 to 4 inclusive;

n is zero, and

Alk denotes a straight alkylene chain of 1 to 3 carbon atoms.

2. Compounds as claimed in claim 1 in which $R_1$ and $R_2$ independently represent hydrogen or methyl or together with the nitrogen atom to which they are attached form a pyrrolidine ring; Alk represents a methylene group; n is zero; Y is =CHNO$_2$ or =NR$_6$, where $R_6$ is nitro, cyano or methylsulphonyl; $R_3$ is hydrogen or methyl; m is 3 and X is oxygen.

3. A compound having formula (Ia);

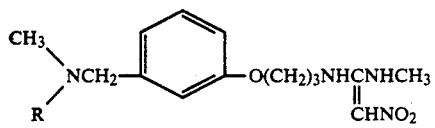

in which R represents hydrogen or methyl, and physiologically acceptable salts thereof, as well as N-oxides and hydrates of such compounds and such salts.

4. A compound as claimed in claim 1 which is N-methyl-N'-[3-[3-(N,N-dimethylaminomethyl)phenoxy]-propyl]2-nitro-1,1-ethenediamine.

5. A compound as claimed in claim 1 which is N-Methyl-N'-[3-[3-(N-methylaminomethyl)phenoxy]-propyl]2-nitro-1,1-ethenediamine.

6. A compound as claimed in claim 1 which is N-Methyl-N'-[3-[3-(1-pyrrolidinylmethyl)phenoxy]-propyl]2-nitro-1,1-ethenediamine.

7. A compound as claimed in claim 1 which is N-nitro-N'-[3-[3-(N,N-dimethylaminomethyl)phenoxy]-propyl]guanidine.

8. A compound as claimed in claim 1 which is N-cyano-N'-methyl-N''-[3-[3-(N,N-dimethylaminomethyl)phenoxy]propyl]guanidine.

9. A compound as claimed in claim 1 which is N-Methyl-N'-[3-[3-(N,N-dimethylaminoethyl)phenoxy]-propyl]2-nitro-1,1-ethenediamine.

10. A compound as claimed in claim 1 which is N-Methanesulphonyl-N'-methyl-N''-[3-[3(N,N-dimethylaminomethyl)phenoxy]propyl]guanidine.

11. Pharmaceutical compositions comprising a compound as claimed in claim 1 in association with a pharmaceutically acceptable carrier or diluent, and if desired other active ingredients.

12. Compositions as claimed in claim 11 in a form suitable for oral, topical or parenteral administration or administration by suppository.

13. Compositions as claimed in claim 12 in oral form as tablets.

14. Compositions as claimed in claim 13 in the form of slow release tablets.

15. Compositions as claimed in claim 13 containing 20 to 200 mg of active ingredient per tablet.

16. Compositions as claimed in claim 12 in topical form as a spray, ointment or cream.

17. A method of treating a condition mediated through histamine H$_2$-receptors which comprises administering to a patient an effective amount of a compound as claimed in claim 1 to relieve said condition.

18. A method as claimed in claim 17 in which the condition is peptic ulceration.

19. A method as claimed in claim 17 in which the condition is an allergic skin condition.

* * * * *